United States Patent
Troetzschel et al.

(10) Patent No.: US 8,494,635 B2
(45) Date of Patent: Jul. 23, 2013

(54) METHOD FOR SINTERING ELECTRICAL BUSHINGS

(75) Inventors: Jens Troetzschel, Bruchkoebel (DE); Goran Pavlovic, Schaafheim (DE); Harald Manhardt, Bruchkoebel (DE); Norbert Wollenberg, Grosskrotzenburg (DE); Nicole Guebler, Friedberg (DE)

(73) Assignee: W. C. Heraeus GmbH, Hanau (DE)

( * ) Notice: Subject to any disclaimer, the term of this patent is extended or adjusted under 35 U.S.C. 154(b) by 248 days.

(21) Appl. No.: 13/018,847

(22) Filed: Feb. 1, 2011

(65) Prior Publication Data

US 2011/0190885 A1 Aug. 4, 2011

(30) Foreign Application Priority Data

Feb. 2, 2010 (DE) .......... 10 2010 006 690

(51) Int. Cl.
*A61N 1/00* (2006.01)

(52) U.S. Cl.
USPC ............ 607/37; 607/116; 607/117; 607/118; 607/119

(58) Field of Classification Search
None
See application file for complete search history.

(56) References Cited

U.S. PATENT DOCUMENTS

| | | | |
|---|---|---|---|
| 4,352,951 A | 10/1982 | Kyle | |
| 4,362,792 A | 12/1982 | Bowsky et al. | |
| 4,456,786 A | 6/1984 | Kyle | |
| 4,678,868 A | 7/1987 | Kraska et al. | |
| 4,737,601 A | 4/1988 | Gartzke | |
| 4,774,953 A | 10/1988 | Foote | |
| 4,816,621 A | 3/1989 | Huebner et al. | |
| 4,991,582 A | 2/1991 | Byers et al. | |
| 4,992,910 A | 2/1991 | Evans | |
| 5,245,999 A | 9/1993 | Dahlberg et al. | |
| 5,272,283 A * | 12/1993 | Kuzma .......................... | 174/262 |
| 5,513,793 A | 5/1996 | Malmgren | |

(Continued)

FOREIGN PATENT DOCUMENTS

| | | |
|---|---|---|
| DE | 69729719 | 7/2005 |
| DE | 102009035971 | 2/2011 |
| DE | 102009035972 | 4/2011 |

OTHER PUBLICATIONS

The Office Action for U.S. Appl. No. 12/850,406 mailed Sep. 17, 2012 (11 pages).

(Continued)

*Primary Examiner* — Brian T Gedeon
*Assistant Examiner* — Ankit Tejani
(74) *Attorney, Agent, or Firm* — Dicke, Billig & Czaja, PLLC

(57) ABSTRACT

One aspect relates to a method for producing an electrical bushing for an implantable device, a corresponding electrical bushing, and a corresponding implantable device. The method according to one embodiment is characterized in that a green blank is produced and sintered from an electrically insulating base body green blank made of a ceramic slurry or powder and at least one electrically conductive bushing body green blank made of a cermet material. The at least one bushing body green blank is inserted into a bushing opening of the base body green blank to form a composite green blank, a shape of the at least one bushing body green blank and a shape of the at least one bushing opening are complementary to each other at least in sections thereof and prevent slippage of the bushing body green blank through the bushing opening. The composite green blank is sintered while applying a force that keeps the bodies together.

9 Claims, 3 Drawing Sheets

U.S. PATENT DOCUMENTS

| | | | |
|---|---|---|---|
| 5,683,435 | A | 11/1997 | Truex et al. |
| 5,738,270 | A | 4/1998 | Malmgren |
| 5,750,926 | A | 5/1998 | Schulman et al. |
| 5,769,874 | A | 6/1998 | Dahlberg |
| 5,782,891 | A | 7/1998 | Hassler et al. |
| 5,821,011 | A | 10/1998 | Taylor et al. |
| 5,851,222 | A | 12/1998 | Taylor et al. |
| 5,866,851 | A | 2/1999 | Taylor et al. |
| 6,284,080 | B1 | 9/2001 | Haq et al. |
| 6,414,835 | B1 | 7/2002 | Wolf et al. |
| 6,586,675 | B1 | 7/2003 | Bealka et al. |
| 6,660,116 | B2 | 12/2003 | Wolf et al. |
| 7,068,491 | B1 | 6/2006 | Burdon et al. |
| 7,107,099 | B1 | 9/2006 | O'Phelan et al. |
| 7,480,988 | B2 | 1/2009 | Ok et al. |
| 7,569,452 | B2 | 8/2009 | Fu et al. |
| 7,668,597 | B2 | 2/2010 | Engmark et al. |
| 7,818,876 | B2 | 10/2010 | Suaning |
| 7,930,032 | B2 | 4/2011 | Teske et al. |
| 7,970,474 | B2 | 6/2011 | Starke |
| 8,000,804 | B1 | 8/2011 | Wessendorf et al. |
| 8,155,743 | B2 | 4/2012 | Rundle et al. |
| 8,163,397 | B2 | 4/2012 | Ok et al. |
| 8,189,333 | B2 | 5/2012 | Foster |
| 2001/0018012 | A1 | 8/2001 | Harmand et al. |
| 2002/0166739 | A1 | 11/2002 | Naerheim |
| 2003/0109903 | A1 | 6/2003 | Berrang et al. |
| 2004/0023101 | A1 | 2/2004 | Jacobson et al. |
| 2004/0128016 | A1* | 7/2004 | Stewart .......... 700/159 |
| 2006/0025866 | A1* | 2/2006 | Serafin et al. ........ 623/23.56 |
| 2006/0247714 | A1 | 11/2006 | Taylor et al. |
| 2007/0041164 | A1 | 2/2007 | Greenberg et al. |
| 2007/0217121 | A1 | 9/2007 | Fu et al. |
| 2009/0281586 | A1 | 11/2009 | Lim |
| 2010/0121438 | A1 | 5/2010 | Jarvik |
| 2011/0032658 | A1 | 2/2011 | Iyer |
| 2011/0034965 | A1 | 2/2011 | Troetzschel et al. |
| 2011/0034966 | A1 | 2/2011 | Troetzschel et al. |
| 2011/0048770 | A1 | 3/2011 | Reiterer et al. |
| 2011/0094768 | A1 | 4/2011 | Davis et al. |
| 2011/0186349 | A1 | 8/2011 | Troetzschel et al. |
| 2011/0232961 | A1 | 9/2011 | Teske |
| 2011/0232962 | A1 | 9/2011 | Teske |

OTHER PUBLICATIONS

The Final Office Action for U.S. Appl. No. 12/850,412 mailed Feb. 25, 2013 (16 pages).

The Office Action for U.S. Appl. No. 12/850,412 mailed Sep. 17, 2012 (11 pages).

The Final Office Action for U.S. Appl. No. 12/850,412 mailed Feb. 25, 2013 (18 pages).

The Restriction Requirement for U.S. Appl. No. 13/018,882 mailed Dec. 20, 2012 (5 pages).

* cited by examiner

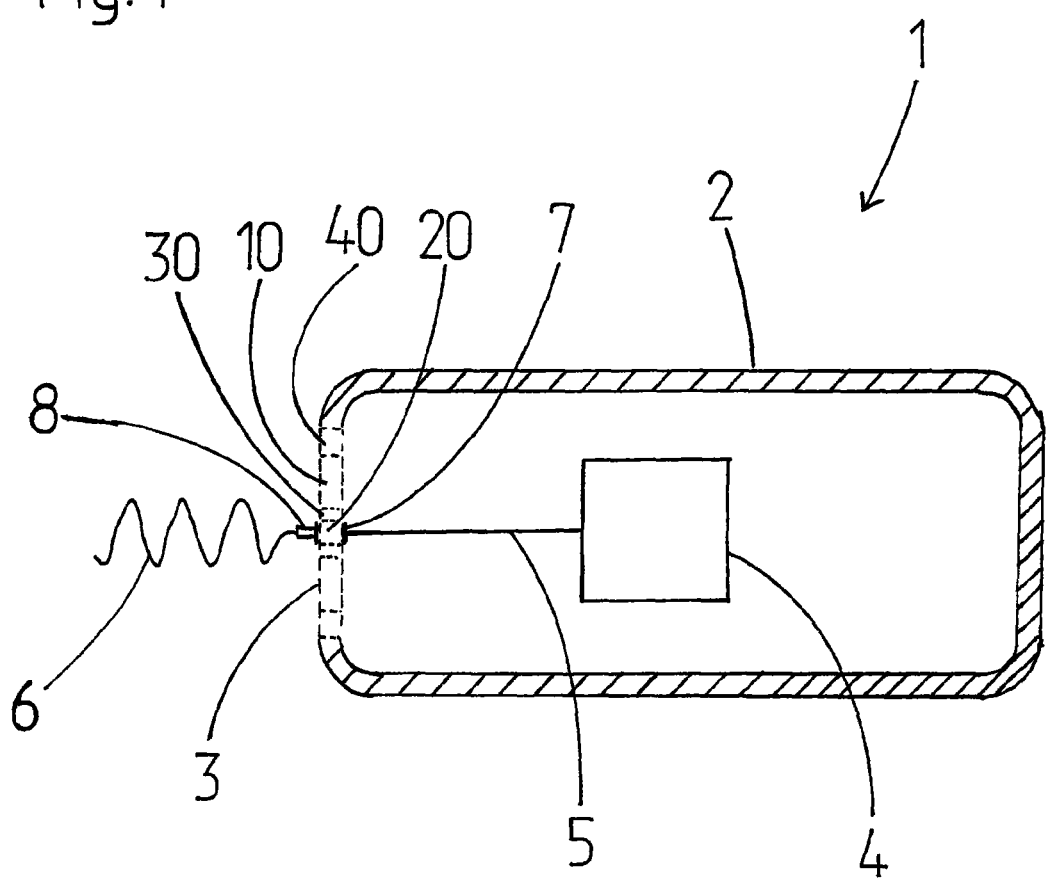

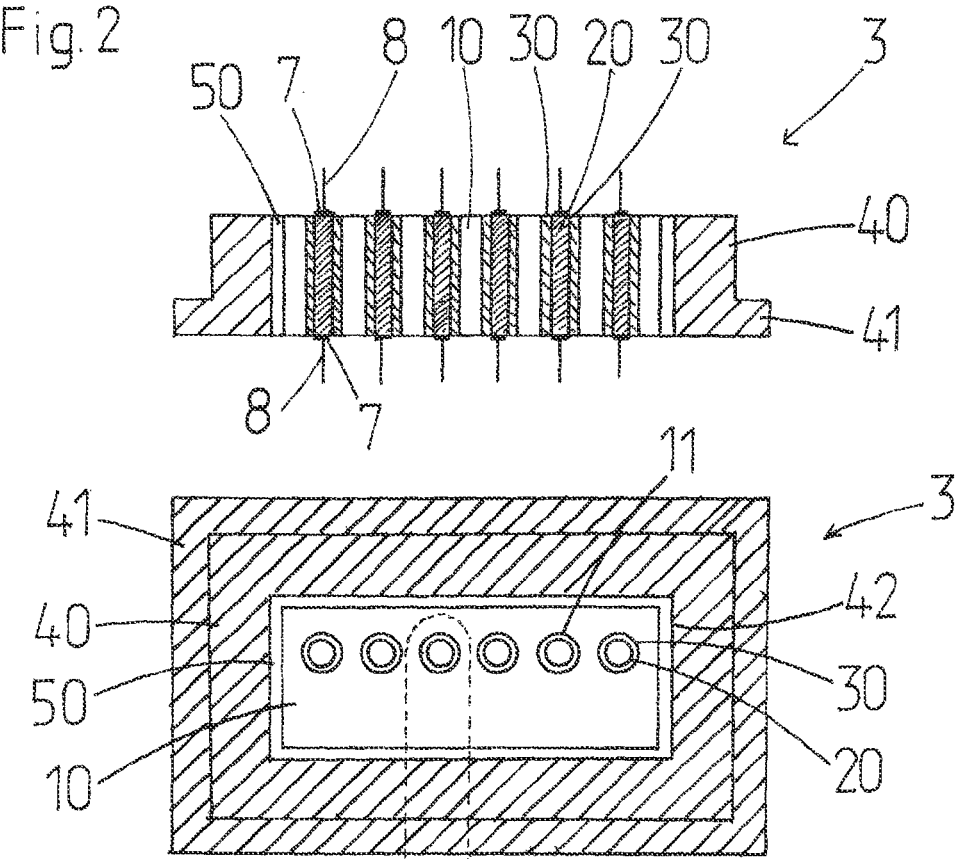
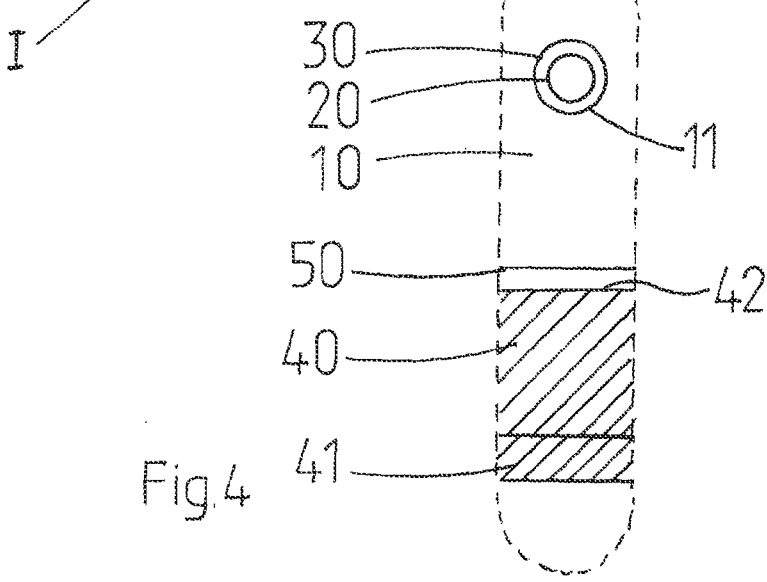

METHOD FOR SINTERING ELECTRICAL BUSHINGS

CROSS-REFERENCE TO RELATED APPLICATIONS

This Utility Patent Application claims priority to German Patent Application No. DE 10 2010 006 690.7, filed on Feb. 2, 2010, which is incorporated herein by reference. This Patent Application is also related to Utility Patent Application filed on even date herewith, entitled "ELECTRICAL BUSHING WITH GRADIENT CERMET" having application Ser. No. 13/018,847,US, which is incorporated herein by reference.

BACKGROUND

One aspect relates to a method for producing an electrical bushing for an implantable device, another to an implantable medical device, another to an electrical bushing as well as to an implantable device.

DE 697 29 719 T2 describes an electrical bushing for an implantable electrical therapeutic device. Electrical bushings of this type serve to establish electrical connection between a hermetically sealed interior and an exterior of the therapeutic device.

Known examples of implantable therapeutic devices include brain pacemakers, cardiac pacemakers or defibrillators. Said devices commonly include a hermetically sealed metal housing which is provided with a connection body, also called header, on one side. Said connection body includes a connection socket that serves for connection of electrode leads, which is effected, for example, by means of a bajonet lock. In this context, the connection socket includes electrical contacts that serve to electrically connect electrode leads to control electronics on the interior of the housing of the implantable device.

Hermetic sealing with respect to a surrounding is an essential prerequisite of a corresponding electrical bushing since the control electronics need to be kept isolated from liquids in order to consistently prevent malfunctions or total failure. Since the conducting wires generally are metal wires or metal pins that are introduced into an electrically insulating ceramic base body of the electrical bushing, the interfaces between the conducting wires and the base body are weak spots. It needs to be ensured, therefore, that the signal-transmitting conducting wires that are introduced into the electrical bushing are introduced into the insulating element such as to be free of gaps.

A gap-free connection between the two elements is commonly generated by metallizing an internal surface of a bore hole in the base body and soldering to it a conducting wire that is guided through it. However, the application of the metallization in the bore hole in the insulating element is a difficult task. Only cost-intensive procedures allow to ensure homogeneous metallization of the internal surface of the bore hole in the insulating element.

For these and other reasons there is a need for the present invention.

SUMMARY

One embodiment is method for producing an electrical bushing for an implantable device characterized in that a green blank is produced and sintered from an electrically insulating base body green blank made of a ceramic slurry or powder and at least one electrically conductive bushing body green blank made of a cermet material. The at least one bushing body green blank is inserted into a bushing opening of the base body green blank to form a composite green blank, a shape of the at least one bushing body green blank and a shape of the at least one bushing opening are complementary to each other at least in sections thereof and prevent slippage of the bushing body green blank through the bushing opening. The composite green blank is sintered while applying a force that keeps the bodies together.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

The invention is described in the following, without limiting its general spirit, by means of exemplary embodiments making reference to the drawings, whereby we wish to explicitly refer to the drawings with regard to any and all details according to the invention that are not elaborated on in more detail in the description. In the figures:

FIG. 1 illustrates a schematic view of an implantable medical device.

FIG. 2 illustrates a schematic cross-sectional view through an electrical bushing according to one embodiment.

FIG. 3 illustrates a schematic top view onto the electrical bushing according to the embodiment illustrated in FIG. 2.

FIG. 4 illustrates a magnified schematic view of a detail of the electrical bushing of FIG. 3.

DETAILED DESCRIPTION

Figure 5:
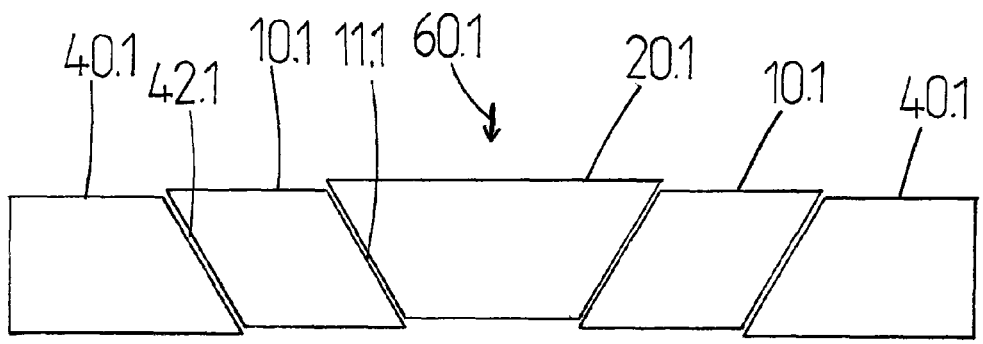
FIG. 5 illustrates a schematic cross-sectional view through shapes that can be used according to one embodiment.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

In the figures below, identical or equivalent elements and/or corresponding parts are denoted with the same reference numbers such that no presentation thereof is provided again herein.

Based on the above-described prior art, one embodiment provides an electrical bushing for an implantable device, and in one embodiment, an implantable medical device, in which the above-mentioned disadvantages are averted and the long-lasting hermetic sealing of the electrical bushing is ensured.

One embodiment is a method for producing an electrical bushing for an implantable device that is developed such that a composite green blank is produced and sintered in the following steps from an electrically insulating base body green blank and at least one electrically conductive bushing body green blank:

- forming the base body green blank from a ceramic slurry or a ceramic powder such as to have at least one bushing opening that extends through the base body green blank;
- forming the at least one bushing body green blank from a cermet slurry, a cermet powder, a metal powder and/or a slurry made of a metal powder, whereby a shape of the at least one bushing body green blank and a shape of the at least one bushing opening are complementary to each other at least in sections thereof and prevent slippage of the bushing body green blank through the bushing opening;
- inserting the at least one bushing body green blank into the at least one bushing opening of the base body green blank to form the composite green blank;
- applying at least one force to the bushing body green blank and/or the base body green blank and sintering the composite green blank while applying the at least one force, whereby the at least one force is directed in the direction of a bracketing of the at least one bushing body green blank in the at least one bushing opening of the base body green blank.

As such, according to one embodiment, both the electrically insulating base body and the electrically conductive bushing body or bodies are constructed from materials capable of being sintered, namely powders and/or slurries based on ceramic materials, cermet and/or hard metals, and sintered jointly. The electrical bushing according to one embodiment represents a simple, biocompatible and long-lasting solution.

In the context of one embodiment, the term, "cermet", refers to a composite material made of ceramic materials in a metallic matrix. In its unprocessed state, it is a mixture of a ceramic powder and a metallic powder. Cermets are characterized by their particularly high hardness and resistance to wear. Cermets are materials that are related to hard metals, but dispense with the hard material, tungsten carbide, and are produced by powder metallurgical means. The sintering process for cermet proceeds alike the one for homogeneous powders. At identical compression force, the metal is compacted more strongly than the ceramic material. Compared to sintered hard metals, a cermet-containing positional element illustrates higher resistance to thermal shock and oxidation. The ceramic components of the cermet in most cases are aluminum oxide ($Al_2O_3$) and zirconium dioxide ($ZrO_2$), whereas niobium, molybdenum, titanium, cobalt, zirconium, and chromium are preferred in one embodiment as metallic components.

The material to be used according to one embodiment can be a dry powder that is compressed into a green blank in the dry state and possesses sufficient adhesion to maintain its compressed green blank shape. In the context of one embodiment, a slurry is a suspension of particles of a powder made of one or more material(s) in a liquid binding agent, commonly in water or in an organic binding agent. A slurry possesses high viscosity and is easy to shape into a green blank without having to apply high pressure.

In the case of green blanks made from slurries, the sintering process, which is generally carried out below the melting temperature of the ceramic, cermet or metal materials that are used, but in individual cases can also be carried out just above the melting temperature of the lower melting component of a multi-component mixture, this usually being the metal component, leads to the binding agent slowly diffusing from the slurry. Overly rapid heating leads a rapid increase of the volume of the binding agent by transition to the gas phase and destruction of the green blank or formation of undesired defects in the work-piece.

During sintering, sintering necks are formed between the particles of the green blank which effects firmly bonded connection of the particles to each other. Simultaneously, the particles of the material move closer together which reduces the size of hollow spaces between said particles until hermetic sealing of the sintered work-piece with respect to gases and liquids is attained. The work-piece shrinks during this process.

It is known that cermet-containing slurries, due to their metal fraction, are subject to more extensive shrinking during the sintering than pure ceramic slurries. Accordingly, there is a risk that the bushing body shrinks more strongly during the sintering than the pure ceramic base body such that no hermetic sealing of the two is established. This is solved according to one embodiment by means of the selection of the shapes of the openings and/or of the green blank bodies that are introduced into the openings as well as by application of a force.

The, at least in sections thereof, complementary shapes of the openings and/or bodies include at least one region that prevents slippage of the bushing body green blank through the base body green blank and/or the bushing opening thereof By means of the application of a force according to one embodiment, which effects a bracketing of the bushing body in the bushing opening of the base body, contact between the complementary surfaces of the base body green blank and the bushing body green blank is effected for the entire duration of the sintering process on which a sintered connection can form regardless of any shrinkage of the green blanks during the sintering.

The formation of a firmly bonded connection along the interface between the base body and the bushing body during the sintering is accelerated if the shrinking process slows down or has come to a standstill. A hermetic sintered connection between the two bodies is thus ensured.

In one embodiment, the at least one force is provided as a weight force that acts on the composite green blank. Said weight force is in one embodiment generated by a weight being placed thereon. A force can also be applied, according to one embodiment, to the green blank by hydraulic or pneumatic pressing or spring pressure.

An electrically conductive connection is established if the metal content of the cermet is in one embodiment 80% or more, and in another embodiment is 90% or more.

In one embodiment, after completing the sintering, at least one surface of the electrical bushing is polished and contacted to a metallic pin or wire in at least one place of the surface at which a bushing body is arranged, a stable and hermetically sealed electrical bushing is attained. The contacting is effected by means of soldering or welding, whereby in one embodiment laser welding and resistance welding lead to long-lasting contacting that conducts the electric current well. The contacting is effected by metallic wires or pins. Alternatively, the bushing body can be provided to be projecting beyond the electrical bushing and/or the base body and itself form a contacting pin. This means provides for current flow from one side of the bushing conductor to the other side.

For integration of an electrical bushing into a housing of an implantable device, one embodiment provides, in addition, for a wreath-shaped fringe body green blank having a receiving opening for the base body green blank into which the base body green blank is inserted in order to form the composite green blank to be formed from a cermet slurry or a cermet powder, whereby an external shape of the base body green blank and a shape of the receiving opening of the fringe body green blank are complementary to each other, at least in sections thereof, and prevent slippage of the base body green blank through the receiving opening. Sintered from a fringe body green blank, a fringe body of this type represents a connection to and/or a termination with respect to the metallic housing of an implantable device.

For this purpose, it is preferred in one embodiment to apply at least one force, in one embodiment weight force, to the fringe body green blank and/or the base body green blank and to sinter the composite green blank while applying the at least one force, whereby the at least one force is directed in the direction of a bracketing of the base body green blank in the receiving opening of the fringe body green blank. Said procedure is associated with the same advantages as those described in relation to the combination of base body green blank and bushing body green blank.

In one embodiment, one or more plies of transitional layers made of a cermet slurry and having a metal fraction that decreases from the bushing body green blank towards the base body green blank are arranged between the at least one bushing body green blank and the base body green blank. A transitional layer consists of a cermet having a metal fraction of approx. 20% to approx. 70%. The metal fraction gradient thus attained ensures that the local shrinkage of the material during the sintering process changes only gradually such that the shifting of the individual bodies with respect to each other during the sintering is further suppressed and a reliable hermetic connection is produced. Affording the same advantage, one embodiment provides for one or more plies of transitional layers made of a cermet slurry or a cermet powder and having metal fractions that decrease from the fringe body green blank towards the base body green blank to be arranged between the fringe body green blank and the base body green blank.

One embodiment is an electrical bushing for an implantable device having an electrically insulating base body and at least one electrically conductive bushing body that is embedded in at least one bushing opening that extends through the base body, whereby the base body is produced from a sintered ceramic material, and which electrical bushing is developed such that the at least one bushing body is made of a sintered cermet material or a sintered metallic material, whereby the base body and the at least one bushing body include a firmly bonded sintered connection.

Hereinafter, the part of the electrical bushing that was produced by means of a sintering process from a base body green blank, a bushing body green blank, including one or more transitional layers, if applicable, as well as from a fringe body green blank, shall be referred to as base body, as bushing body and/or as fringe body, respectively, even if these are provided firmly bonded in one work-piece in the electrical bushing according to one embodiment.

The electrical bushing according to one embodiment is advantageous in that, due to the sintering process of the adjacent bodies, a hermetic, firmly bonded, sintered connection exists that includes both a desired transition from electrically insulating to electrically conductive, as well as the desired impermeability for gases and liquids.

In one embodiment, the base body is connected circumferentially through a firmly bonded sintered connection to a wreath-shaped fringe body made of a cermet material, whereby the fringe body includes a receiving opening, in which the base body is arranged. The fringe body ensures stable and hermetic connection to the housing of an implantable device.

In one embodiment, the electrical bushing is hermetically sealed for gases and liquids.

In one embodiment, the at least one bushing body and the at least one bushing opening in the base body and/or the base body and the receiving opening in the fringe body, at least sections thereof, have complementary shapes that prevent slippage of the bushing body through the bushing opening and/or of the base body through the receiving opening. This also applies to the green blanks on which the respective bodies are based. A suitable complementary shape, at least in sections, has an essentially V-shaped, L-shaped, T-shaped and/or Z-shaped cross-section. These shapes, which can also be combined with each other, prevent slippage of the one body through the opening of the other.

The electrical bushing according to one embodiment can be or is produced according to any one of the methods according to the embodiments described above.

One embodiment is an implantable device, or an implantable medical device, having an electrical bushing according to the embodiments of the type described above.

Features, advantages, and details specified in the context of one of the subject matters of one embodiment is shall also apply to the respective other subject matters of other embodiments.

FIG. 1 illustrates a schematic view of an implantable medical device 1, for example a brain pacemaker, a cardiac pacemaker or a defibrillator. The device 1 includes a metallic and biocompatible housing 2 having an electrical bushing 3. An electronic measuring and control device 4 is arranged on the interior of the housing 2 and is connected to an electrically conductive bushing body 20 of the electrical bushing 3 by means of a connecting wire 5 and an electrical contact 7. On the exterior of the bushing body 20, there is, beyond another electrical contact, a contact pin 8 to which a conducting coil 6, indicated schematically only, is attached that is connected to a stimulation electrode.

The electrical bushing 3 hermetically seals an opening in housing 2. In electrical bushing 3, the bushing body 20 is framed sequentially by transitional layers 30 and a base body 10, which includes on its circumference a fringe body 40 next to which the housing 2 is situated. The electrically insulating base body 10 prevents short-circuiting between the electrically conductive, extended conducting wire 5 and the metallic housing 2 and/or the fringe body 40 which is also partly metallic.

The base body 10 is made from an insulating composition of materials. Electrical signals proceeding through the conducting wire 5 are not to be attenuated or short-circuited by contacting the housing 2 of the implantable device 1. Moreover, the base body 10 must include a biocompatible composition to be suitable for medical implantation. For this reason, it is preferred in one embodiment for the base body 10 to consist of a glass-ceramic or glass-like material. Compositions of base body 10 materials that include at least one from the group, aluminum oxide ($Al_2O_3$), magnesium oxide (MgO), zirconium oxide ($ZrO_2$), aluminum titanate ($Al_2TiO_5$), and piezoceramic materials, are preferred in some embodiments. Said substances possess high electrical resistance and low dielectric losses. In addition, these properties are complemented by high thermal resistance and good biocompatibility.

Biocompatible metals include, in some embodiments, metals from the group, titanium (Ti), tantalum (Ta), iridium (Ir), niobium (Nb), platinum (Pt) or an alloy including at least one of these metals.

The insulating composition of materials is a powder mass that illustrates at least minimal adhesion of the powder particles. This is commonly implemented in that a grain size of the powder particles does not exceed 0.5 mm. In this context, the green blank is produced either by compaction of powder masses or by shaping and subsequent drying. Green blanks of an insulating base body 10 and of electrically conductive bushing bodies 20 and, if applicable, of a fringe body 40 are produced in parallel, placed inside each other and fired subsequently.

FIG. 2 illustrates a schematic cross-section of an electrical bushing 3 according to one embodiment. The electrical bushing 3 includes a circumferential fringe body 40 that has been sintered from a cermet material and has a flange 41. Situated next to it towards the inside, there is a transitional layer 50 made of a cermet with a lower metal fraction than that of the fringe body 40, followed by a base body 10 made of a non-conductive, purely ceramic material.

Bushing bodies 20 are embedded in the base body 10 and jacketed each with a transitional layer 30. The transitional layer 30 consists of a cermet with a metal content of approx. 20% to approx. 70%, whereas the bushing body includes a higher metal content and, and in one embodiment, consists entirely of a sintered metallic material. Since the entire part illustrated in FIG. 2 is sintered, it represents a hermetic and stable electrical bushing 3.

The fringe body 40 includes a flange 41, whereby the flange, in one embodiment, is metallically conductive. The flange serves to seal the electrical bushing with respect to a housing 2 of the implantable device 1. The electrical bushing 3 is held in the implantable device 1 by the fringe body 40. The flange 41 forms a bearing that can be engaged by a lid of the implantable medical device 1, in one embodiment preferably in a sealing manner. Accordingly, the fringe body 40 having the flange 41 can have a U- or H-shaped cross-section. Integrating at least one flange 41 into the fringe body 40 ensures secure, shock-resistant, and long-lasting integration of the electrical bushing 3 in the implantable device 1. In addition, the flange can be provided such that a lid of the implantable device 1 is connected to the fringe element 40 in a non-positive fit and/or positive fit manner.

FIG. 3 illustrates a schematic top view of the electrical bushing 3 according to the embodiment as illustrated in FIG. 2. Proceeding from outside to inside, the flange 41, the fringe body 40, a transitional layer 50, the base body 10, and, embedded therein, six bushing bodies 20 that are arranged next to each other and are each provided with a transitional layer 30 are illustrated. FIG. 3 also illustrates where a receiving opening 42 of the fringe body 40 for the base body 10, as well as a bushing opening 11 in the base body 10 for a bushing body 20, are situated.

FIG. 4 illustrates in more detail a detail of FIG. 3 that corresponds to the dashed lines and reference signs I from FIG. 3. Accordingly, FIG. 4 illustrates the layered structure of the electrical bushing 3. In this context, it is preferable in one embodiment to assemble the various bodies into a green blank and sinter them jointly.

Figure 6:
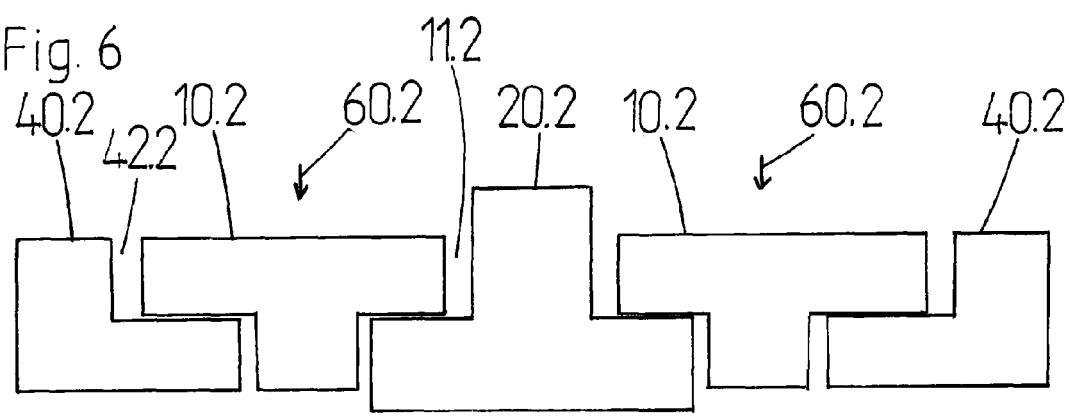
FIG. 6 illustrates another schematic cross-sectional view through shapes that can be used according to one embodiment.
Figure 7:
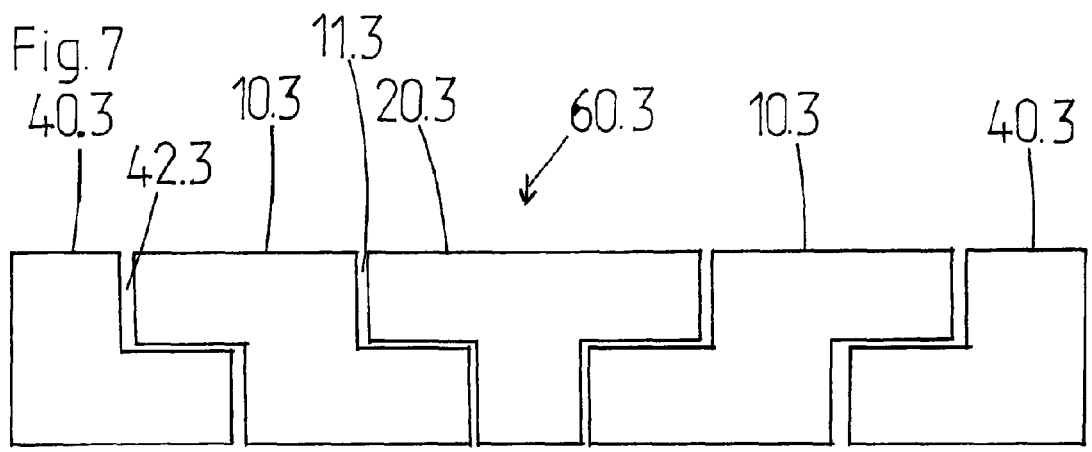
FIG. 7 illustrates a third schematic cross-sectional view through shapes that can be used according to one embodiment.

FIGS. 5 to 7 illustrate three exemplary embodiments of selections of body shapes, according to one embodiment, of green blanks used and of suitable points for the application of a force.

FIG. 5 illustrates an essentially V-shaped arrangement, in which, on the outside, a fringe body green blank 40.1 having a slanting internal wall is illustrated schematically, next to which a base body green blank 10.1 with a diamond-shaped cross-section is situated. The slants are mirrored on the left and right of a bushing body green blank 20.1 in central arrangement. The bushing body green blank 20.1 itself has a trapezoidal cross-section.

As is evident from FIG. 5, the various green blank bodies are arranged staggered upwards in vertical direction proceeding from outside towards inside since the total width of the base body green blank 10.1 and of the bushing body green blank 20.1 is larger than the total width of the receiving opening 42.1 of the fringe body green blank 40.1 prior to the sintering. The same is true of the width of the central bushing body green blank 20.1 with respect to the width of the bushing opening 11.1 in the base body green blank 10.1

During sintering, a weight force 60.1, which follows gravity to act downwards, is applied to the central bushing body green blank 20.1. If the bushing body green blank 20.1 is heavy enough, its own weight force is sufficient. Accordingly, the bushing body green blank 20.1 is pushed into the bushing opening 11.1 and the base body bushing body green blank 20.1 10.1 is pushed into the receiving opening 42.1.

Due to the V-shaped arrangement of the openings and green blanks, the green blanks in central arrangement cannot slip through the fringe body bushing body greenling 20.1. Simultaneously, the application of a force provides for continual contact of the opposite surfaces of the fringe body green blank 40.1, base body green blank 10.1, and bushing body green blank 40.1 during the entire sintering process.

If the various green blanks are subject to a shrinking process during the sintering, the bushing body green blank 20.1 and the base body green blank 10.1 slip downward due to the effect of the weight force 60.1 until, ideally, they are flush with the fringe body green blank 40.1 In the process, they keep forming sintering necks that lead to connection of the various bodies. A large number of sintering necks and thus a secure connection is formed and no longer terminated by slippage, in one embodiment, if the shrinking process ceases.

FIG. 6 illustrates an exemplary embodiment, in which the bushing body green blank 20.2 is inverse T-shaped, whereas the base body green blank 10.2 has an upright T-shaped cross-section. The fringe body green blank 40.2 is L-shaped. The bars of the L- and T-shaped structures lie on each other. A weight force 60.2 is being applied to the base body green blank 10.2. On the side(s), the green blank bodies have some play with respect to each other. This is the case, for example, if the green blank bodies are fabricated to initially fit each other, but lose in width during the sintering because of shrinkage such that gaps 42.2/42.3 and 11.2/11.3 arise. Due to the continual application of a weight force 60.2, the surfaces of the bars that lie on of each other are in continual contact with each other during the sintering and form a hermetic sinter connection.

The same effect is attained in the exemplary embodiment according to FIG. 7, whereby the base body green blank 10.3 has a Z-shaped cross-section. In this case, the bushing body green blank 20.3 is upright T-shaped and has a weight force 60.3 applied to it in central position. Accordingly, the T-shaped bushing body 20.3 is pushed onto the Z-shaped base body 10.3, which, in turn, is pushed onto the L-shaped fringe body 40.3 such that a hermetic sinter connection is formed on all horizontal connection surfaces.

All specified features, including those evident from the drawings only, as well as individual features that are disclosed in combination with other features are considered essential for the embodiments both alone and in combination. Embodiments according to the invention can be provided through individual features or a combination of multiple features. Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. A method for producing an electrical bushing for an implantable device, whereby a composite green blank is produced and sintered from an electrically insulating base body green blank and at least one electrically conductive bushing body green blank, the method comprising:

forming the base body green blank from a ceramic slurry or a ceramic powder such as to have at least one bushing opening that extends through the base body green blank;

forming the at least one electrically conductive bushing body green blank from a cermet slurry, a cermet powder, a metal powder and/or a slurry made of a metal powder, whereby a shape of the at least one electrically conductive bushing body green blank and a shape of the at least one bushing opening are complementary to each other at least in sections thereof and prevent slippage of the electrically conductive bushing body green blank through the at least one bushing opening;

inserting the at least one electrically conductive bushing body green blank into the at least one bushing opening of the base body green blank to form the composite green blank; and applying at least one force to the electrically conductive bushing body green blank and/or the base body green blank and sintering the composite green blank while applying the at least one force, whereby the at least one force is directed in a direction of a bracketing of the at least one bushing body green blank in the at least one bushing opening of the base body green blank.

2. The method according to claim 1, characterized in that the at least one force is provided as a weight force that acts on the composite green blank.

3. The method according to claim 2, characterized in that the weight force that acts on the composite green blank is generated by a weight being placed thereon.

4. The method according to claim 1, characterized in that, after completing the sintering, at least one surface of the electrical bushing is polished and contacted to a metallic pin or wire in at least one place of the surface at which the bushing body is arranged.

5. The method according to claim 1, characterized in that a wreath-shaped fringe body green blank having a receiving opening for the base body green blank into which the base body green blank is inserted in order to form the composite green blank is formed from a cermet slurry or a cermet powder, whereby an external shape of the base body green blank and a shape of the receiving opening of the fringe body green blank are complementary to each other, at least in sections thereof, and prevent slippage of the base body green blank through the receiving opening.

6. The method according to claim 5, characterized in that at least one force is applied to the fringe body green blank and/or the base body green blank and the composite green blank is sintered while applying the at least one force, whereby the at least one force is directed in the direction of a bracketing of the base body green blank in the receiving opening of the fringe body green blank.

7. The method according to claim 1, characterized in that one or more plies of transitional layers made of a cermet slurry and having a metal fraction that decreases from the bushing body green blank towards the base body green blank are arranged between the at least one bushing body green blank and the base body green blank.

8. The method according to claim 5, characterized in that one or more plies of transitional layers made of a cermet slurry or a cermet powder and having metal fractions that decrease from the fringe body green blank towards the base body green blank are arranged between the fringe body green blank and the base body green blank.

9. A method for producing an implantable device comprising:

forming an electrically insulating base body green blank from a ceramic slurry or a ceramic powder such as to have at least one bushing opening that extends through the base body green blank;

forming at least one electrically conductive bushing body green blank from a cermet slurry, a cermet powder, a metal powder and/or a slurry made of a metal powder, whereby a shape of the at least one electrically conductive bushing body green blank and a shape of the at least one bushing opening are complementary to each other at least in sections thereof and prevent slippage of the bushing body green blank through the bushing opening;

inserting the at least one bushing body green blank into the at least one bushing opening of the base body green blank to form a composite green blank; and applying at least one force to the bushing body green blank and/or the base body green blank and sintering the composite green blank while applying the at least one force, whereby the at least one force is directed in a direction of a bracketing of the at least one bushing body green blank in the at least one bushing opening of the base body green blank.

* * * * *